United States Patent [19]

Batty

[11] Patent Number: 5,673,431
[45] Date of Patent: Oct. 7, 1997

[54] FACE MASK SAFETY SHIELD

[75] Inventor: Joe Allen Batty, Chillicothe, Ohio

[73] Assignee: Dwight A. Marshall, Worthington, Ohio

[21] Appl. No.: 519,364

[22] Filed: Aug. 25, 1995

[51] Int. Cl.$^6$ .................................................. A41D 13/00
[52] U.S. Cl. ........................................ 2/9; 2/10; 2/11
[58] Field of Search ............................... 2/8, 9, 15, 10, 2/11, 12, 424

[56] References Cited

U.S. PATENT DOCUMENTS

| | | | |
|---|---|---|---|
| 2,277,090 | 3/1942 | Feiler | 2/8 |
| 2,729,820 | 1/1956 | Anderson | 2/9 |
| 2,731,637 | 1/1956 | Kaplan et al. | 2/9 |
| 2,926,406 | 3/1960 | Edwards et al. | 24/68 |
| 2,978,709 | 4/1961 | Atha | 2/9 |
| 3,074,072 | 1/1963 | Edwards et al. | 2/8 |
| 3,214,767 | 11/1965 | Weber | 2/9 |
| 3,214,809 | 11/1965 | Edwards | 24/68 |
| 3,254,932 | 6/1966 | Blaney | 2/8 |
| 3,517,392 | 6/1970 | Hodge et al. | 2/8 |
| 3,579,638 | 5/1971 | Davis et al. | 2/8 |
| 3,866,244 | 2/1975 | Ruck | 2/8 |
| 3,868,727 | 3/1975 | Paschall | 2/8 |
| 4,701,965 | 10/1987 | Landis | 2/9 |
| 4,821,341 | 4/1989 | Baptiste | 2/10 |
| 5,440,760 | 8/1995 | Highsmith | 2/9 |

*Primary Examiner*—Michael A. Neas
*Attorney, Agent, or Firm*—Dwight A. Marshall

[57] ABSTRACT

A face mask safety shield structure having a shield support formed of a fire-retardant material with an adjustable head band for adjusting the structure to fit various sizes of user heads. A visor is attached to opposite sides of the shield and enables a user to raise the visor from a frontal horizontal position with respect to the shield support. The structure has a full length lens assembly of a length to fully cover the user's eyes and face and is removably secured to the visor to extend vertically downward from the visor when the visor is in the horizontal position to cover a user's eyes and face. The assembly has a tinted section positioned above a clear section with the tinted section formed to have a length less than the length of the clear section for shielding the eyes of the user. With the visor in the frontal horizontal position the user may look through both the clear and tinted sections and move the visor upward in an arc to swing the lens assembly away from the user's eyes and face.

13 Claims, 2 Drawing Sheets

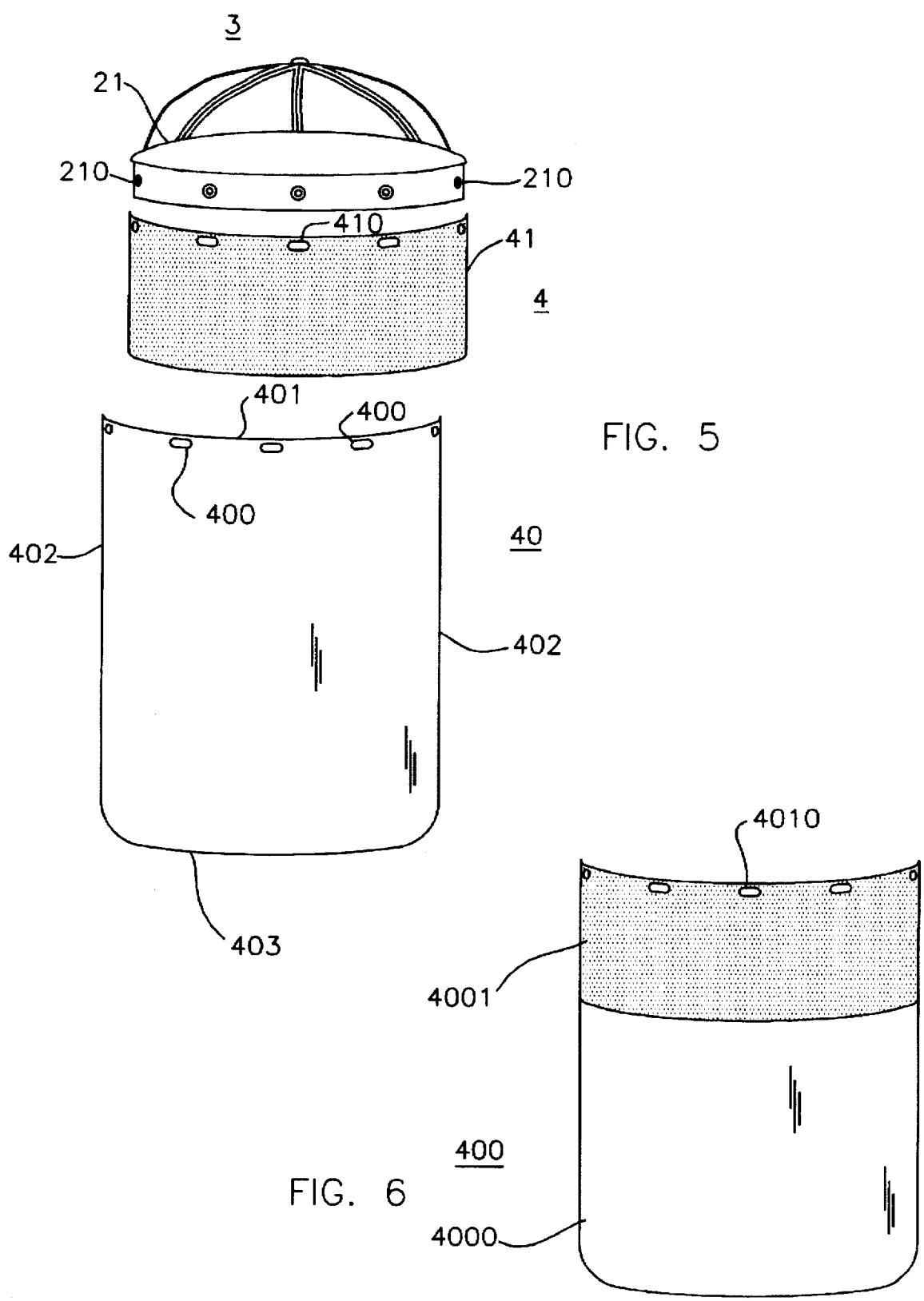

FACE MASK SAFETY SHIELD

TECHNICAL FIELD

The invention relates to safety apparatus and in particular to a face mask safety shield for use to protect a user's head and eyes in various manufacturing operations.

BACKGROUND AND PROBLEM

Grinding and brazing operations are widely used in manufacturing operations to form material according to application specifications. Such operations involve oxygen and acetylene cutting of steel to form various configurations of steel products or to cut steel pieces into scrap. Other operations include oxygen and acetylene brass welding and brazing to join component parts together in various manufacturing applications. Still other operations require that materials be configured into manufactured products by grinding the materials and using electric and air grinders to form the products.

Typically, such operations involve applying heat to the material and products that result in the generation of heat. Such operations also result in the generation of embers and sparks that have the ability to cause injury to operators of equipment used in these operations. In addition, the applied and generated heat cause a glow that makes it difficult for operators to closely examine the material to check progress of the operations.

Equipment operators performing these types of operations oftentimes wear eye goggles that are equipped with tinted lens to both protect the operator's eyes and enable the operator to look at the material during welding, brazing, cutting and grinding operations. However, a problem arises in that such goggles, while protecting the eyes of the operator, do not protect the face of the operator and must be removed to enable the operator to get a clear view of the work. Cumbersome and unwieldy helmet structures are oftentimes used in welding operations and the like to protect both the face and eyes of the operator. Such helmets generally have a mask type of construction with a tinted eye shield and are designed to cover the face of the operator and to fit entirely around the front and side portions of the operator's head with the operator's eyes positioned behind the tinted eye shield. A problem arises in these types of mask helmets in that elaborate structures are required to fit the mask to the operator's head and to enable the mask to be pivoted up about the operator's head and away from the operator's eyes and face so that the operator may have a clear view of the material operations.

Simpler visor structures have been devised to protect the face of a user by the use of a clear shield that extends downward from a front portion of the helmet to cover the face of the wearer. These type of structures, while allowing a clear view of work, have a problem in that tinted goggles are required to be worn over the eyes and beneath the clear visor to protect the user's eyes if they are to be used while operating welding, brazing, cutting and grinding equipment. Helmet structures have also been developed with rotatable partial sun-visors. A problem arises in the use of these types of helmets in that the partial sun-visor does not protect the face and must be pivoted up and away from the face to enable the user to have a clear view of work operations thereby leaving the user's face and eyes unprotected. In addition, elaborate structures are required for adjusting the helmet and visor structures to fit a wide variety of head sizes.

Accordingly, a need exists for a simple face mask safety shield structure that enables users' to have both a clear and tinted view of work operations while protecting both the users' eyes and face and which may be rotated away from a user's face and be easily adjusted to fit a wide variety of head sizes.

SOLUTION

The foregoing problems are solved by a face mask safety shield structure having a movable frontal visor with a lens assembly covering a user's face to protect the user's eyes and face. The structure has a lens assembly formed of a flexible fire-retardant polycarbonate material to have a tinted generally rectangular configured section positioned above a clear section. A length of the tinted section is less than a length of the clear section and is positioned in front of the user's eyes to protect the eyes. The tinted section has a plurality of openings formed along a top surface to secure the lens assembly to the visor thereby enabling eyes of a user to look through both the tinted and clear sections. The frontal visor may be moved from a horizontal position in an arc to swing the lens assembly away from the user's face.

The face mask safety shield structure has a frame formed of a fire-retardant flexible material having a head band with a pair of overlapping ends positioned in a rear portion thereof for adjusting the head band to conform to a head size of the user. A pair of cranial straps each extended upward from the head band are positioned on opposite sides of the head band with devices positioned adjacent the ends for adjustably coupling the straps to support the frame on the user's head with the head band situated in an approximate horizontal position around a forehead of the user.

A semi-circular visor formed of a fire-retardant rigid material with fastening devices positioned along the outer surfaces thereof has ends rotatably attached to opposite sides of the frame head band at the juncture of the cranial straps. Projections each positioned on opposite sides of the frame head band slightly below and in front of the juncture of the cranial straps with the head band engage a cutout located in each end of the visor when visor is lowered and function to maintain the lowered visor in a horizontal position with respect to the frame. The rotatable visor is enabled to be raised in an arc from the horizontal position to swing the lens assembly away from the user's face and eyes.

In one embodiment of the invention, the lens assembly has a member formed of a flexible clear fire-retardant polycarbonate material having a straight top upper edge with a plurality of openings formed along a top surface. Each opening is aligned to correspond with and receive one of the visor fastening devices for removably securing the member to the visor. The lens assembly member extends vertically downward from the visor when the visor is in the horizontal position to cover the user's face and eyes and wrap around the sides of the user's head. In this embodiment, the lens assembly has a component of a generally rectangular configuration formed of a fire-retardant tinted polycarbonate material to which ultra-violet inhibitors may be added and which has a tint range between 4 and 5. The tinted component may have a width corresponding to the upper width of the clear member upper edge and a length less than the length of the clear member. A plurality of openings are formed along a top surface of the tinted component with each opening aligned to correspond with and receive one of the visor fastening devices. The tinted component is removably secured to the visor between the clear member and the visor with the tinted component positioned above a lower clear portion of the lens assembly member to protect the user eyes with the visor in the horizontal position thereby enabling the user to look outward through both the tinted component and lower clear portion.

In another embodiment of the invention the lens assembly is a single piece member of a length to protect the user's eyes and face. The member is formed of a flexible fire-retardant polycarbonate material to have a tinted generally rectangular configured section with a tint range between 4 and 5 positioned above a clear section. The width of the tinted section may correspond to an upper width of the clear section and has a length less than the length of the clear section. A plurality of openings are formed along a top surface of the tinted section with each opening aligned to correspond with and receive one of the visor fastening devices for removably securing the lens assembly member to the visor. With the visor in the horizontal position the one piece lens assembly extends vertically downward from the visor protecting the user's eyes and face and enables eyes of the user to look through both the tinted and clear sections.

In yet another embodiment of the invention, a cap formed of a fire-retardant material with an expansion section positioned in a rear section thereof is assembled over the frame and inside the visor to protect the user's hair and head. A plurality of fasteners are each positioned around an inner surface of a bottom seam for optionally securing the cap to the frame head band covering the frame.

BRIEF DESCRIPTION OF THE DRAWING

FIG. 5 is an exploded view of a clear shield member and tinted lens component assembly intended for mounting on the shield support frame and movable visor set forth in FIGS. 2 and 4, and FIG. 6 sets forth a one piece tinted and clear lens assembly to be assembled to shield support frame in FIGS. 1 and 2.

DETAILED DESCRIPTION

Figure 1:
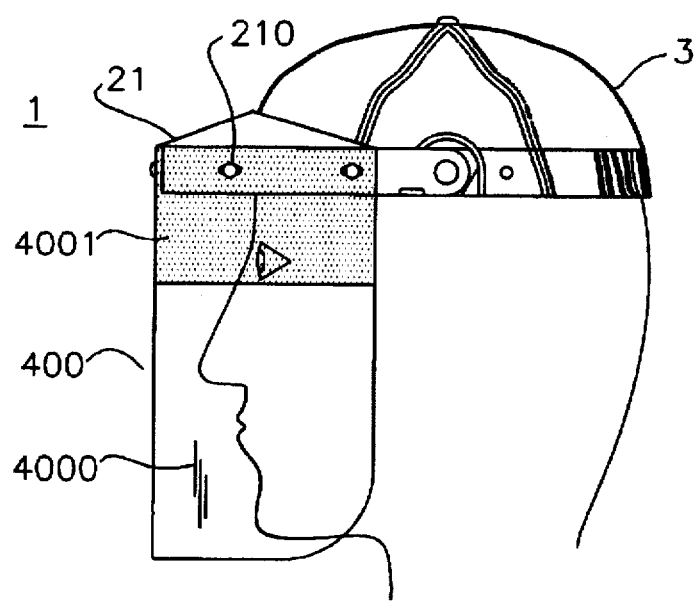
FIG. 1 illustrates a face mask safety shield in accordance with principles of the invention, FIG. 2 sets forth a shield support frame and movable visor used with the face mask safety shield set forth in FIGS. 1 and 4.
Figure 2:
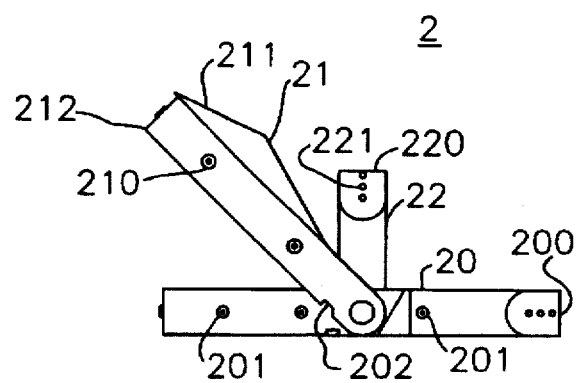

In an exemplary embodiment of the invention, FIG. 1 of the drawing, face mask safety shield structure 1, positioned on the head of a user, has a shield support or frame 2, FIG. 2, mounting a movable frontal visor 21 with shield securing or fastening devices 210 located and positioned thereon. A face shield shown as lens assembly 400, FIG. 1, is fastened to visor 21 and extends vertically downward in front of the user's face and protects the user's eyes and face from embers, sparks and ultra-violet rays generated by various operations such as brazing, cutting, grinding, welding and the like. In one embodiment of the invention, lens assembly 400 is formed of a flexible fire-retardant polycarbonate material to have a tinted section 4001 positioned above a clear section 4000. Tinted section 4001 has a length less than a length of clear section 4000. A plurality of openings is formed along a top surface of tinted section 4001 with each opening aligned to correspond with and receive one of visor securing devices 210. Securing devices 210 secure lens assembly 400 to visor 21 to extend vertically downward from visor 21 when visor 21 is in a horizontal position with tinted section 4001 positioned in front of the user's eyes and with clear section 4000 wrapped around and covering the user's face. Thus, lens assembly 400 protects the user's eyes and face and also enables the user to look through both tinted section 4001 and clear section 4000. Rotating visor 21 upward along an arc path swings lens assembly 400 away from in front of the user's face.

Face mask safety shield structure 1 has a one piece shield support, frame 2, FIG. 2, formed of a fire-retardant flexible material having a head band 20 with a pair of overlapping ends 200 positioned in a rear portion. Each of the head band ends 200 may be provided with a wide array of fastening devices that are used to adjust head band 20 to conform to a head size of the user. For example, male and female snaps may be affixed to ends 200 and fastened together to adjust the size of head band 20. In another configuration, holes may be located in one of the ends 200 and protuberances located on the opposite end such that ones of the protuberances can be inserted in selected ones of the holes to adjust the head band size. Frame 2 also has a pair of cranial straps 22 each extended upward from head band 20 on opposite sides thereof with fastening devices 221 positioned adjacent ends 220 such that cranial straps 22 may be adjustably coupled, FIG. 4, to fit a user's or wearer's head with head band 20 situated in an approximate horizontal position around the user's forehead. Although frame 2 may be formed from a one piece pattern it is to be understood that frame 2 may be molded of a semi-rigid fire retardant material by use of a mold or similar device. Furthermore, frame 2 may be a combination of head band 20 and cranial straps 22 connected in various manners to form frame 2. A number of fasteners 201 may optionally be positioned along an outside surface of head band 20 for use in attaching a covering cap 3, FIG. 3, to frame 2 to protect the hair and top of the user's head.

Figure 4:
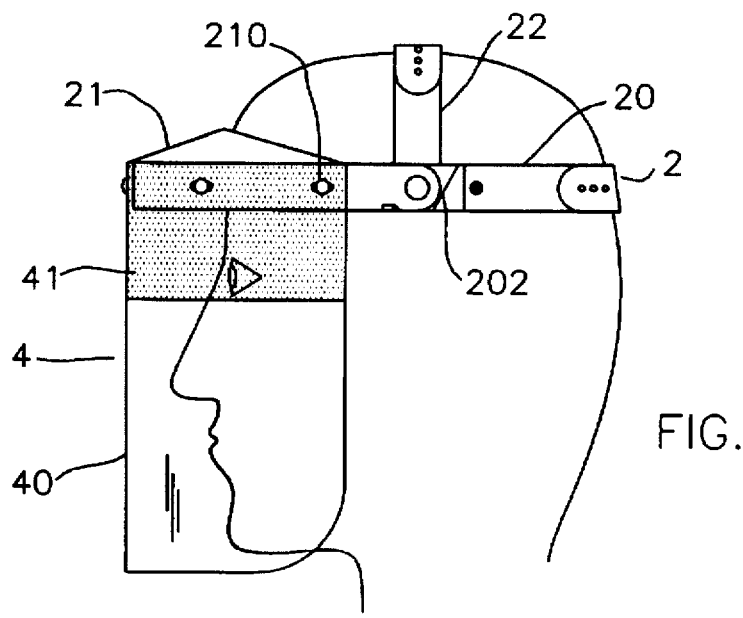
FIG. 4 illustrates another version of the face mask safety shield set forth in FIG. 1 in accordance with principles of the invention.

Visor 21, used to mount lens assemblies 400 and 4, FIGS. 1 and 4, respectively, onto frame 2, FIG. 2, is a semi-circular member formed of a molded fire-retardant rigid material with a lower curved flat surface 212 positioned beneath an upper curved section 211. Fastening devices 210 are positioned along outer surface of lower curved flat surface 212. Fastening devices 210 may be a variety of devices such as threaded metal inserts so that screws may be used to removably fasten lens assemblies, 400 and 4, FIGS. 1 and 4, respectively, onto visor 21. Other types of fastening devices 210, FIG. 2, may also be used. For example, right angled handle devices may be rotatably mounted in curved flat surface 212 and turned in one direction to fit into openings of lens assemblies 400, 4 and turned in another direction to secure lens assemblies 400, 4 to visor 21. Ends of visor 21 are rotatably attached to opposite sides of head band 20 at a juncture of cranial straps 22 with head band 20 thereby enabling visor 21 to be raised upward in an arc from a horizontal position. Head band 20 is formed with a pair of projections 202 each positioned on opposite sides of head band 20 slightly below and in front of the juncture of cranial straps 22 with head band 20. A cutout located in each end of visor 21 receives a corresponding one of projections 202 when visor 21 is lowered as shown in FIGS. 1 and 4 and functions to maintain lower visor 21 in the horizontal position with respect to frame 2 while enabling visor 21 to be raised in an arc to swing lens assemblies 400, 4 away from the user's face and eyes.

Figure 3:
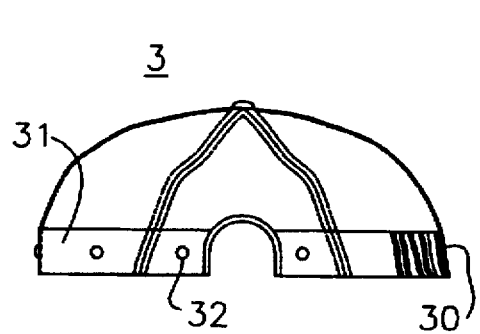
FIG. 3 illustrates an optional cap used in conjunction with the shield support and visor set forth in FIG. 1 to protect a user's head as shown in FIG. 1.

An optional shielding coveting, FIG. 1, may be used with frame 2, FIG. 2, to protect the hair and the top of a user's head. It is to be understood that such a coveting may be a light plastic helmet structure, not shown, or a type of cap 3, FIG. 3, that may be fastened to head band 20, FIG. 2, coveting frame 2. Cap 3, FIG. 3, is formed of a fire-retardant material such as a flexible plastic, cloth or canvas material with an expansion section 30 positioned in a rear section thereof. A plurality of fasteners 32 such as snaps or the like, may each be positioned around an inner surface of cap 3 or along a bottom seam 31 to correspond with head band fasteners 201, FIG. 2, for use in securing cap 3 to head band 20 and cover frame 2 as shown in FIG. 1 of the drawing.

In an embodiment of the invention, lens assembly 4, FIGS. 4 and 5, has a full length face shielding member 40 formed of a one piece flexible clear fire-retardant polycarbonate material. Shield member 40 is formed of a sheet of the material to have a configuration of a straight top upper edge 401 with a pair of opposite side edges 402 positioned at right angles with respect to upper edge 401. Each side edge 402 has rounded corners extending into a lower edge 403 positioned parallel to upper edge 401. Side edges 402 are formed of a length, FIG. 4, sufficient to cover the face of a user. In a typical configuration, shielding member 40 has a length in the range of 9 to 10 inches (22.86 to 25.4 centimeters) and a upper edge width of 15 to 16 inches (38.1 to 40.64 centimeters). Depending upon particular applications in which lens assembly 4 is to be used, member 40 may be, but not necessarily limited thereto, formed to have a thickness of a range from 3 mil. to 1.27 centimeters. A plurality of openings 400 are formed along a top surface of member 40 with each opening 400 aligned to correspond with and receive one of visor fastening devices 210. Member 40 may thereby be removably secured to visor 21 by fastening devices 210 with lens assembly 4 extended vertically downward from visor 21 when visor 21 is in the horizontal position to cover the user's face and eyes. With member 40 secured or fastened to semi-circular visor 21, shielding member 40 extends around visor 21 to cover and protect both sides of the user's face.

In this embodiment of the invention, lens assembly 4 has a tinted component 41 positioned within lens assembly 4 to protect the user's eyes but still enable users to lower their eyes and look through clear shield member 40. Component 41 has a generally rectangular configuration formed of a fire-retardant tinted polycarbonate material to have a tint range between 4 and 5. Ultra-violet inhibitors may be added to the material to protect the user's eyes from ultra-violet rays that may emanate from an article on which the user is working. Component 41 may have, although not necessarily limited thereto, a width corresponding to the upper width of member 40 and has a length less than the length of member 40. Typically, component 41 may have a width of 15 to 16 inches (38.1 to 40.64centimeters), or less, and a length of 2 to 3 inches (5.08 to 7.62 centimeters). A plurality of openings 410 are formed along a top surface of component 41 with each opening 410 aligned with member 40 openings 400 to correspond with and receive one of visor fastening devices 210. Visor fastening devices 210 removably secure tinted component 41 to visor 21 between shield member 40 and visor 21 with tinted component 41 positioned above a lower clear portion of member 40 to protect the user eyes and still enable the user to glance down through the clear portion of member 40. Lens assembly 4 extends down from visor 21 when visor 21 is in the horizontal position to protect the user's eyes and face and may swing upward and away from the user's by movement of visor 21. Although component 41 is shown to have a width of that of the upper edge of member 40 it is to be understood that other widths are within the teaching of the invention. Also in accordance with the invention, component 41 may be secured to visor 21 with shield member 40 positioned between component 41 and visor 21.

In another embodiment of the invention, FIGS. 1 and 6, a single piece lens assembly member 400 is intended to be fastened or secured to visor 21 and extend vertically downward from visor 21 when visor 21 is in the horizontal position to protect the eyes and face of the user. Lens assembly member 400, having the above set forth dimensions of shielding member 40, FIG. 5, is of a length to protect the user's eyes and face and is formed of a flexible fire-retardant polycarbonate material having a thickness in a selected range of 3 mil. to ½ inch (1.27 centimeters). One piece member 400, FIG. 6, is formed to have a tinted generally rectangular configured section 4001 with a tint range between 4 and 5 positioned above a clear section 4000 and generally has a width corresponding to an upper width of clear section 4000. Tinted section 4001 may have ultra-violet inhibitors added thereto to protect the user's eyes from ultra-violet rays and is of a length less than a length of clear section 4000. Typically, tinted section 4001 may have a length of 2 to 3 inches (5.08 to 7.62 centimeters) as compared to a length of 6 to 8 inches (15.24 to 20.32 centimeters) of clear section 4000. A plurality of openings 4010 are formed along a top surface of tinted section 4001 with each opening 4010 aligned to correspond with and receive one of visor fastening devices 210, FIG. 1. Fastening devices 210 are provided for removably securing lens assembly member 400 to visor 21 such that lens assembly member 400 extends vertically downward from visor 21 when visor 21 is in the horizontal position thereby protecting the user's face and enabling eyes of the user to look through both tinted and clear sections 4001, 4000, respectively. Although FIG. 6, shows that tinted section 4001 has a width equal to the width of clear section 4000 it is to be understood that the width of tinted section could be less thereby leaving clear strips alongside the vertical edges of tinted section 4001. Face mask safety shield structure is constructed such that one frame 2, FIG. 2, can be used with a wide number of lens assemblies 400, 4 for various applications.

SUMMARY

It is obvious from the foregoing that the facility, economy and efficient of face mask safety shields may be substantially enhanced by a structure having a movable frontal visor with removable lens assemblies covering a user's face to protect the user's eyes and face and which is formed of a flexible fire-retardant polycarbonate material to have a tinted lens section positioned above a clear lens section thereby enabling eyes of a user to look through both the tinted and clear sections without removing the shield structure.

I claim:

1. A face mask safety shield structure comprising a one piece shield support formed of a fire-retardant material having an adjustable head band and cranial straps for adjusting the structure to fit the head of a user and wherein said head band has a pair of projections each positioned on said head band below and in front of said cranial straps, a visor having a plurality of fastening devices each positioned along a lower curved flat surface of said visor rotatably attached to opposite sides of said shield support at a juncture of said head band with said cranial straps for enabling said visor to be raised from a frontal horizontal position with respect to said shield support and wherein said visor has a pair of cutouts located adjacent opposite ends thereof and located on a lower edge of said visor corresponding with said head band projections for each receiving one of said head band projections for maintaining said visor in the frontal horizontal position, and a lens assembly having a configuration of a straight top upper edge with a pair of opposite side edges positioned at right angles with the upper edge and having rounded corners extending into a lower edge parallel to the upper edge and of a length and width to protect a user's eyes and face and removably secured to said visor by said fastening devices to extend vertically downward from said visor when said visor is in the frontal horizontal position for shielding the user's face and having a tinted section positioned above a clear section with a length less than a length of said clear section for shielding the user's eyes when said visor is in the frontal horizontal position and for enabling the user to look through both said clear and tinted sections.

2. The face mask safety shield structure set forth in claim 1 wherein said shield support comprises a one piece frame formed of a fire-retardant flexible material having said head band with a pair of overlapping ends positioned in a rear portion for adjusting said head band to conform to a head size of the user and having a pair of cranial straps each extended upward from said head band on opposite sides thereof with devices positioned adjacent ends thereof for adjustably coupling said cranial straps for supporting said frame on the user's head with said head band situated in the horizontal position around a forehead of the user's head.

3. The face mask safety shield structure set forth in claim 2 wherein said visor comprises a semi-circular member formed of a fire-retardant rigid material with said fastening devices positioned along outer surfaces thereof and having ends rotatably attached to said opposite sides of said head band at the juncture of said cranial straps with said head band for enabling said visor to be raised upward from the horizontal position in an arc with respect to said frame.

4. The face mask safety shield structure set forth in claim 3 wherein said lens assembly comprises a member formed of a flexible clear fire-retardant polycarbonate material having a straight top upper edge with a plurality of openings formed along a top surface thereof with each opening aligned to correspond with and receive one of said visor fastening devices for securing said clear member to said visor with said clear member extended vertically downward from said visor when said visor is in the frontal horizontal position to cover the user's face and eyes.

5. The face mask safety shield structure set forth in claim 4 wherein said lens assembly comprises a component having a generally rectangular configuration formed of a fire-retardant tinted polycarbonate material to have a tint range between 4 and 5 with ultra-violet inhibitors added thereto and with a width corresponding to an upper width of said clear member upper edge and a length less than a length of said clear member and having a plurality of openings formed along a top surface thereof with each opening aligned to correspond with one of said clear member openings and receive one of said visor fastening devices for removably securing said tinted component to said visor between said clear member and said visor with said tinted component positioned above a lower clear portion of said clear member to protect the user eyes.

6. The face mask safety shield structure set forth in claim 3 wherein said lens assembly comprises a member of a length to protect the user's face and formed of a flexible fire-retardant polycarbonate material to have a tinted generally rectangular configured section with a tint range between 4 and 5 positioned above a clear section with a width corresponding to an upper width of said clear section and a length less than a length of said clear section and having a plurality of openings formed along a top surface of said tinted section with each opening aligned to correspond with and receive one of said visor fastening devices for securing said lens assembly member to said visor thereby enabling eyes of the user to look through both said tinted and clear sections.

7. The face mask safety shield structure set forth in claim 2 further comprising a cap formed of a fire-retardant material with an expansion section positioned in a rear section thereof and having a plurality of fasteners each positioned around an inner surface of a bottom seam for securing said cap to said head band and covering said frame.

8. A face mask safety shield structure comprising a frame formed of a fire-retardant flexible material having an adjustable head band with snaps positioned around an outer edge thereof and having a pair of cranial straps each extended upward from said head band on opposite sides thereof with devices positioned adjacent ends thereof for adjustably joining said straps for supporting said head band about a user's head, a semi-circular visor formed of a fire-retardant rigid material with fasteners positioned around outer surfaces thereof and having ends rotatably attached to said opposite sides of said head band at a juncture of said cranial straps with said head band for enabling said visor to be raised in an arc from a horizontal position with respect to said frame, a shield member formed of a flexible clear fire-retardant polycarbonate material having a plurality of openings formed along a top surface thereof with each opening aligned to correspond with and receive one of said visor fasteners for securing said shield member to said visor with said shield member extended vertically downward from said visor when said visor is in the horizontal position to cover the user's face and eyes, a tinted lens member having a generally rectangular configuration formed of a fire-retardant tinted polycarbonate material with a length less than a length of said shield member and having a plurality of openings formed along a top surface thereof with each opening aligned to correspond with and receive one of said visor fasteners for securing said tinted lens member to said visor between said shield member and said visor to protect eyes of the user while enabling the user to look through both said clear shield and tinted lens members, and a cap formed of a fire-retardant material with an expansion section in a rear section thereof and having a plurality of snaps each positioned around an inner surface of a lower seam to correspond with ones of said frame snaps for securing said cap to said head band and covering said frame.

9. A face mask safety shield structure comprising a one piece frame formed of a fire-retardant flexible material having an adjustable head band with fasteners positioned around an outer surface thereof and having a pair of cranial straps each extended upward from said head band on opposite sides thereof with devices positioned adjacent ends thereof for adjustably coupling said straps for supporting said frame on a user's head with said head band positioned around a forehead of the user, a semi-circular visor formed of a fire-retardant rigid material with securing devices positioned around outer surfaces thereof and having ends rotatably attached to said opposite sides of said head band at a juncture of said cranial straps with said head band for enabling said visor to be raised in an arc from a horizontal position with respect to said frame, a shield member of a length to protect a user's face and formed of a flexible fire-retardant polycarbonate material to have a tinted generally rectangular configured section positioned above a clear section with a length less than a length of said clear section and having a plurality of openings formed along a top surface of said tinted section with each opening aligned to correspond with and receive one of said visor securing devices for securing said shield member to said visor to extend vertically downward from said visor when said visor is at the horizontal position to protect the face of the user and thereby enable eyes of the user to look through both said tinted and clear sections, and a cap formed of a fire-retardant material with an expansion section in a rear section thereof and having a plurality of fasteners each positioned around in an inner surface of a lower seam of said cap to correspond with and engage ones of said head band fasteners for securing said cap to said head band with said cap covering said frame.

10. A face mask safety shield structure comprising a one piece frame formed of a fire-retardant flexible material having an adjustable head band with a pair of cranial straps each extended upward from said head band on opposite sides thereof with devices positioned adjacent ends thereof for adjustably joining said straps for supporting said frame on a user's head with said head band positioned around a forehead of a user's head and wherein said head band has a pair of projections each positioned on said head band below and in front of said cranial straps, a semi-circular visor formed of a fire-retardant rigid material with fastening devices positioned around outer edges thereof and having ends rotatably attached to said opposite sides of said head band at a juncture of said straps with said head band for enabling said visor to be raised in an arc from a horizontal position with respect to said frame and wherein said visor has a pair of cutouts located adjacent opposite ends thereof and on a lower edge of said visor corresponding with said head band projections for each receiving one of said head band projections for maintaining said visor in the frontal horizontal position, and a shield member formed of a flexible clear fire-retardant polycarbonate material having a generally rectangular configuration of a straight top edge with a pair of opposite side edges positioned at right angles with the upper edge and having rounded corners extending into a lower edge parallel to the upper edge and having a plurality of openings formed along a top surface thereof with each opening aligned to correspond with and receive one of said visor fastening devices for securing said clear shield member to said visor to extend vertically downward from said visor to protect the user's face when said visor is in the horizontal position, and a lens member having a generally rectangular configuration of an upper edge corresponding with said straight top edge of said shield and with a pair of opposite side edges positioned at right angles with the upper edge and having rounded corners extending into a lower edge parallel to the upper edge and formed of a fire-retardant tinted polycarbonate material with a length less than a length of said clear shield member and having a plurality of openings formed along a top surface thereof with each opening aligned to correspond with and receive one of said visor fastening devices for removably securing said lens member to said visor between said clear shield member and said visor thereby enabling a user to look through both said tinted lens and clear shield members.

11. A face mask safety shield structure comprising a one piece frame formed of a fire-retardant flexible material having an adjustable head band with a pair of cranial straps each extended upward from said head band on opposite sides thereof with devices positioned adjacent ends thereof for adjustably coupling said cranial straps for supporting said frame on a user's head with said head band positioned around the forehead of the user and wherein said bead band has a pair of projections each positioned on said head band below and in front of said cranial straps, a semi-circular visor formed of a fire-retardant rigid material with securing devices positioned around outer surfaces thereof and having ends rotatably attached to said opposite sides of said head band at a juncture of said cranial straps with said head band for enabling said visor to be raised in an are from a horizontal position with respect to said frame and wherein said visor has a pair of cutouts located adjacent opposite ends thereof and on a lower edge of said visor corresponding with said head band projections for each receiving one of said head band projections for maintaining said visor in the frontal horizontal position, and a lens assembly of a length and width for protecting the face of the user and formed of a flexible fire-retardant polycarbonate material to have a configuration of a straight top upper edge with a pair of opposite side edges positioned at fight angles with the upper edge and having rounded corners extending into a lower edge parallel to the upper edge to have a tinted generally rectangular configured section positioned above a clear section with a width corresponding to an upper width of said clear section and a length less than a length of said clear section and having a plurality of openings formed along a top surface of said tinted section with each opening aligned to correspond with and receive one of said visor securing devices for securing said lens assembly to said visor to extend vertically downward from said visor when said visor is in the horizontal position thereby protecting the user's eyes and face and enabling the user to look through both said tinted and clear sections.

12. A face mask safety shield structure comprising a shield support formed of a fire-retardant material having an adjustable head band and a pair of cranial straps for adjusting said shield support to fit a user's head and wherein said head band has a pair of projections each positioned on said head band below and in front of said cranial straps, a visor rotatably attached to opposite sides of said shield support at a juncture of said head band with said cranial straps enabling said visor to be raised in an arc from a frontal horizontal position with respect to said head band and having a pair of cutouts located adjacent opposite ends thereof and on a lower edge of said visor corresponding with said head band projections for each receiving one of said head band projections for maintaining said visor in the frontal horizontal position, a shield member of a length for protecting the user's face and formed of a fire-retardant clear polycarbonate material removably secured to said visor to extend vertically downward from said visor when said visor is in the frontal horizontal position to cover the user's face, and a lens member formed of a tinted polycarbonate material having ultra-violet inhibitors therein and with a width corresponding to an upper width of said clear shield member and with a length less than a length of said clear shield member and removably secured to said visor between said visor and a top surface of said clear shield member for protecting the eyes of a user and enabling the user to look through both said tinted lens and clear shield members when said visor is in the frontal horizontal position.

13. A face mask safety shield structure comprising a shield support formed of a fire-retardant material having an adjustable head band for adjusting said shield support to fit a user's head, a visor rotatably attached to opposite sides of said shield support for enabling said visor to be raised in an arc from a horizontal position with respect to said shield support, a shield member of a length for protecting the user's face and formed of a clear polycarbonate material removably secured to said visor to extend vertically downward in front of the user's face when said visor is in the horizontal position, a lens member formed of a tinted polycarbonate material with a width corresponding to an upper width of said clear shield member and a length less than the length of said clear shield member and removably secured to said visor between said visor and a top surface of said clear shield member for protecting eyes of the user and enabling the user to look through both said clear shield and tinted lens member when said visor is in the horizontal position, and a cap formed of a fire-retardant material with an expansion section in a rear section thereof and secured to said shield support for covering said shield support and protecting the user's head.

* * * * *